(12) United States Patent
Ito et al.

(10) Patent No.: US 6,437,002 B1
(45) Date of Patent: Aug. 20, 2002

(54) AGENT FOR PREVENTING AND TREATING SKIN DISEASES

(75) Inventors: Shinobu Ito; Eiji Ogata; Hiroshi Ikeno, all of Tokyo (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/418,317

(22) Filed: Oct. 14, 1999

Related U.S. Application Data

(63) Continuation of application No. PCT/JP99/02516, filed on May 14, 1999.
(60) Provisional application No. 60/104,157, filed on Oct. 14, 1998, provisional application No. 60/104,159, filed on Oct. 14, 1998, and provisional application No. 60/104,160, filed on Oct. 14, 1998.

(30) Foreign Application Priority Data

| May 15, 1998 | (JP) | ............................................. 10-133479 |
| May 15, 1998 | (JP) | ............................................. 10-133480 |
| May 15, 1998 | (JP) | ............................................. 10-133481 |
| Jun. 29, 1998 | (JP) | ............................................. 10-182353 |
| Jun. 29, 1998 | (JP) | ............................................. 10-182354 |
| Jun. 29, 1998 | (JP) | ............................................. 10-182355 |

(51) Int. Cl.$^7$ .............................................. A61K 31/00
(52) U.S. Cl. ..................................................... 514/724
(58) Field of Search ......................................... 514/724

(56) References Cited

U.S. PATENT DOCUMENTS 5,646,190 A  7/1997 Martin ........................ 514/724

5,965,750 A  * 10/1999 Oonishi et al. .............. 549/218

FOREIGN PATENT DOCUMENTS

| DE | WO 95/05852 | 3/1995 | |
| JP | 7316079 | 12/1995 | |
| JP | 08151334 | 6/1996 | |
| JP | 09110268 | 4/1997 | |
| JP | 9-110628 | 4/1997 | ............ A61K/7/00 |
| JP | 09278726 | 10/1997 | |
| JP | 10095733 | 4/1998 | |

* cited by examiner

*Primary Examiner*—Zohreh Fay
(74) *Attorney, Agent, or Firm*—Sughrue Mion, PLLC

(57) ABSTRACT

The present invention relates to an agent for preventing and treating skin diseases comprising as an active ingredient an ascorbic acid derivative which is a compound represented by the following formula (1) or a salt thereof and which per se exhibits no anti-oxidation activity but is capable of transforming in vivo into a compound having an anti-oxidation activity;

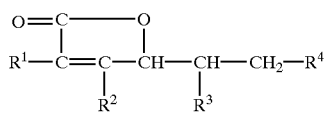

(1)

wherein $R^1$ represents a group capable of bonding to the carbon at the 2-position of the ascorbic acid skeleton through an ether or ester bond and transformable in viv into a hydroxyl group, and $R^2$ to $R^4$ may be the same or different and each represents a hydroxyl group or a group derived therefrom.

46 Claims, No Drawings

AGENT FOR PREVENTING AND TREATING SKIN DISEASES

CROSS REFERENCE TO RELATED APPLICATIONS

This application is a continuation application of earlier filed PCT Application PCT/JP99/02516, filed May 14, 1999, the benefit of the filing date of which is claimed pursuant to 35 U.S.C. §120, and the disclosure of which is incorporated herein by reference. Benefit pursuant to 35 U.S.C. §119(e)(i) of the filing dates of Provisional Application Nos. 60/104,157 filed Oct. 14, 1998, 60/104,159 filed Oct. 14, 1998 and 60/104,160 filed Oct. 14, 1998 pursuant to 35 U.S.C. §111(b) is claimed.

TECHNICAL FIELD

The present invention relates to an agent for preventing and treating skin diseases comprising an ascorbic acid derivative, a composition containing the agent and a preparation containing the agent, each of which has an effect of preventing and/or treating skin diseases and is employable in various forms such as a medical product, a quasi-drug and a cosmetic material.

BACKGROUND ART

Various agents for preventing and treating skin diseases, which have effects of preventing and/or treating skin diseases such as comedos, atopic skin diseases and wounds, have been developed heretofore.

The comedo is sometimes called pimple or acne vulgaris and means those having disorders or symptoms described in the following publication. That is, Kosho Kaishi (*Journal of Perfumes and Cosmetics*), Vol. 21, No. 4, page 341 (1997) describes comedos stating that "The comedo (acne) is a chronic inflammation disease attacking folliculus pili of sebaceous gland. This is generated predominantly at the age of puberty and a large number of intrinsic and extrinsic factors are complicatedly combined to form the cause of disease. With respect to the mechanism in the crisis of comedos, importance is attached to *Propionbacterium acnes* (hereinafter simply referred to as *P. acnes*). It is considered that irritation or destruction of the folliculus pili is brought about particularly in the process of inflammation from comedo to red papula, pustule, induration or cystoma by the action of various enzymes as a product of *P. acnes*, such as lipase, protease and hyaluronidase, or as a result of release of lysosome enzyme from neutrophiles reached folliculus pili due to a neutrotaxis factor produced from *P. acnes*."

The mechanism in the crisis of comedos is not yet clearly elucidated but sthenia of sebum cutaneum, sthenia in the keratinization of hair follicle, proliferation of bacteria and inflammation of hair follicle wall are considered to be main causes. Heretofore, comedos have been treated using a cream or ointment having blended thereto a sebum secretion inhibitor, a keratinization inhibitor (keratin abrasive), an antimicrobial or an antiinflammatory according to the cause. However, existing comedo treating agents having blended thereto a drug of various types have problems.

For example, the sebum secretion inhibitor used is a female hormone and the side effects brought about by the hormone agent raise serious problems. The keratinization inhibitor (keratine abrasive) includes a sulfur compound and a salicyclic acid and these are very problematic ingredients because of their excessive drying property or irritativeness. The antimicrobial includes chlorhexydine gluconate and benzalkonium chloride and these have a strong irritation and cause extreme chapping of the skin, thus, the effect cannot be satisfactorily brought out in the actual use.

The existing antiinflammatories have not yet succeeded in achieving satisfactory treatment of comedos. It is also considered to use a drug having a different action in combination and synergistically bring out the comedo treating effect, however, the synergistic effect obtained is not sufficient or side effects are synergistically caused. Thus, no effective combination of drugs for the comedo treatment has been attained. Moreover, even if the above-described drugs successfully treat comedos, comedo vestiges such as pigmentation or cratered skin impression remain for a long period of time and this causes a serious psychic problem particularly for young peoples at the age of puberty.

The combination use of an antimicrobial such as chlorhexydine gluconate or benzalkonium chloride and a sebum secretion inhibitor conventionally used in the treatment of comedos cannot attain a satisfactory synergistic effect as verified in the Comparative Example described later.

The atopic skin disease is one of allergic reactions. The allergic reactions are classified into Types I to IV by the mechanism in the action and various diseases are considered to occur due to secondary or composite participation of one or more of these Types. Out of these Types, Type I and Type IV, particularly Type IV, seem to participate in atopic skin diseases. Type I is sometimes called immediate allergy in which an antibody participates and Type IV is sometimes called delayed allergy in which cell-mediated immunity participates. Thus, these two Types greatly differ in the operation mechanism. Heretofore, for the treatment of atopic skin diseases, antihistaminics, steroid agents and the like have been used, however, antihistaminics having an effect only on Type I do not exhibit sufficiently high potency to atopic skin diseases and moreover, some cause adverse reaction affecting the center. Steroid agents having an effect also on Type IV exhibit high potency but due to their heavy adverse reaction, very great care is disadvantageously required on use of steroid agents. As such, a non-steroid type drug having effects on Type I and Type IV allergies, being low toxic and exhibiting excellent potency on atopic skin diseases has been keenly demanded.

The wound healing process in general can be classified into three overlapping stages. The first stage is a period of inflammation which takes place over the first three days after the tissue is injured. The second stage is a period of granule tissue formation which takes place in the term of 3 to 12 days after the injury. The third stage is a period of matrix formation and reorganization which take place in the term of about 3 to about 6 days after the injury. In the inflammation period, upon injuring of a tissue, blood ingredients are released into the wound region, whereby the coagulation cascade is activated and a matrix is provided against inflow of inflammable cells. Thereafter, formation of granule tissues starts such that new blood vessel systems embedded in a matrix generally known as an extracellular matrix (ECM) which is a loose matrix comprising fibroblast, macrophages, collagen, fibronectin and hyaluronic acid, are densely grouped to organize the granule tissue. The epithelial cell in the wound grows and new blood vessels are formed (vascularization) to supply nutrients and oxygen to the injured region. This supply of nutrients is indispensable for the synthesis, deposition and organization of ECM.

Within few hours after injury, re-epitheliarization starts to completely recover the injured surface. This matrix formation and reorganization stage is initiated at the same time of gradual lysis of granule tissues resulting from devascularization and involves disappearance of cells, fibronectin and type III collagen. The granule tissue is replaced by a connective tissue organized by a frame of a collagen and an elastin fibers which provide strength and elasticity to the tissue, respectively. This frame is then saturated with proteoglycans and glycoproteins. Thus, the reorganization is accompanied by synthesis of new collagen and decomposition of aged collagen. After the matrix formation and reorganization, scared tissues finally result.

Another most important aspect in the healing of a wound is the rate of the wound gaining a tensile strength. During the wound healing, the tensile strength increases in proportion to the increase of the collagen content in the wound. The increment of the tensile strength correlates to the collagen synthesis rate over the initial 10 weeks in the healing of a wound.

In many studies, it has been stressed that an ascorbic acid is a matter of importance in the healing of wounds. The ascorbic acid is concentrated at the wound to be healed and the circulation level thereof is abruptly reduced after the skin injury. Furthermore, the ascorbic acid is indispensable for the growth and maintenance of connective tissues. The ascorbic acid is a cofactor of several kinds of endogenous hydroxylases including propylhydroxylase and xylylhydroxylase which hydroxylate propyl in procollagen polypeptide and a lysyl residue to form hydroxyproline and hydroxylysine, respectively. The hydroxyproline is essential for the maximum stabilization of triple helices and accordingly, secretion of procollagen from cells is indispensable. On the other hand, the hydroxylysine participates into the cross-link formation and moreover acts as an active site of the covalent bond of galactosyl or a glucosyl-galactosyl residues at the time of biosynthesis of collagen. Furthermore, the ascorbic acid stimulates the peroxidation of lipid and in turn, stimulates the synthesis of collagen.

In general, wounds are healed by taking an initial treatment of using an antiinflammatory, a styptic and an involucrin-forming ingredient in many cases. By applying such a treatment, the reorganization of skin tissues can be accelerated and keloid or the like can be prevented from generating afterward.

However, such a healing method has a problem in that the healing of a wound takes a time and the wound scar changes into keloid or the like in many cases.

The wound healing method in general includes a method of accelerating the growth of epidermic cells, a method of using an antibiotic or an antiinflammatory to prevent infectious diseases or inflammation and thereby allow the healing to proceed spontaneously, and a method of grafting skin. According to the method of accelerating the growth of epidermic cells, a factor capable of activating the epidermic cell is administered, however, solcoseryl which is a representative activation factor [see, Oyo Yakuri (*Applied Pharmacology*), Vol. 22, No. 4, pp. 565–579 (1981) and Qyo Yakuri (*Applied Pharmacology*), Vol. 22, No. 3, pp. 433–442 (1981)] is extracted from placenta or young cattle and thus, the isolation and purification thereof is difficult. As a result, the drug obtained is expensive.

The method of using an antibiotic or an antiinflammatory to prevent infectious diseases or inflammation and thereby allow the healing to proceed spontaneously is disadvantageous in that the antiphlogistic ingredient such as a salicylic acid derivative-type antiphlogistic, an aniline derivative-type antiphlogistic, antispasmodic, a pyrazolone-type antiphlogistic, an indomethacin-based antiphlogistic, a mefenamic acid-based antiphlogistic, an antihistamine agent, an antiallergic agent and an inflammation-liking enzymatic steroid agent, is in itself not a fundamental healing method and moreover, after the healing, there arises a problem such that stretched feeling is generated or scar or keloid is formed.

The method of grafting skin is useful for burns in a high degree, however, since an operation is necessary, this method is not used for general wounds or bedsores and when used, the treatment fee is tremendously high. In general, wounds by a scald or burn is healed by cooling the wound region with flowing water in the initial treatment. By applying such a treatment, necrosis or edema of skin tissues can be minimized and generation of keloid or the like after the treatment can be prevented.

The cooling with flowing water has a problem in that the diseased part must be dipped in flowing water or contacted with flowing water and the human body is disadvantageously prevented from moving or acting. A method of cooling the diseased part with ice or an ice pack also has a problem that movement or action of the human body is hindered, similarly to the cooling with water.

The method for healing scalds or burns accompanied with a grave skin injury includes a method of accelerating the growth of epidermic cells, a method of using an antibiotic or an antiinflammatory to prevent infectious diseases or inflammation and thereby allow the healing to proceed spontaneously, and a method of grafting skin. According to the method of accelerating the growth of epidermic cells, a factor capable of activating the epidermic cell is administered, however, solcoseryl which is a representative activation factor [see, Oyo Yakuri (*Applied Pharmacology*), Vol. 22, No. 4, pp. 565–579 (1981) and Oyo Yakuri (*Applied Pharmacology*), Vol. 22, No. 3, pp. 433–442 (1981)] is extracted from placenta or young cattle and thus, the isolation andpurification thereof is difficult. As a result, the drug obtained is expensive.

On the other hand, it is said that ascorbic acid has an effect of preventing stain or freckle ascribable to sunburn.

As an example of use of ascorbic acid for skin diseases, a comedo treating composition using an antioxidant is proposed in, for example, U.S. Pat. No. 5,646,190, and it is described that vitamin C is employable as the antioxidant. In Japanese Patent Laid-Open Publication No. 110628/1997, it is described that a composition containing an ascorbic acid is effective for seborrhea or excessive sebum secretion, and the examples reveal that a cream or a gel containing an ascorbic acid is effective for inhibition of excessive sebum secretion.

However, an ordinary L-ascorbic acid is liable to be oxidatively decomposed, and a preparation formed therefrom is also unstable and cannot endure the practical use as it is. Further, the ordinary L-ascorbic acid has such poor stability that it is difficult t for preparation therefrom. Besides, the ordinary L-ascorbic acid frequently causes irritation and inflammation on the skin because of acidity, and hence any desirable effect cannot be found even when it is used for skin diseases such as comedos, atopic skin diseases and wounds. Therefore, derivatives of ascorbic acid have been recently used in quasi-drugs and cosmetics.

In Japanese Patent Laid-Open Publication No.95733/1998, for example, a comedo treating agent containing a phosphate diester compound of ascorbic acid and tocopherol is proposed. In National Publication of International Patent No. 501925/1997, a composition containing an antioxidant, which is employable for the treatment of skin diseases, is described and vitamin C derivatives such as ascorbyl palmitate and ascorbyl magnesium phosphate are set forth as examples of the antioxidants.

The phosphate diester compound of ascorbic acid and tocopherol, however, hardly exhibits an ascorbic acid activity when absorbed through the skin. That is to say, although such ascorbic acid derivatives have scarcely any side effect and are safe, they cannot exhibit an ascorbic acid activity sufficiently in the living human body, and a satisfactory effect cannot be expected. There is another problem that an ascorbic acid derivative in which the carbon at the 2-position is not esterified or etherified is liable to be oxidatively decomposed and is unstable similarly to the ascorbic acid.

In other words, it is found that conventional L-ascorbic acid derivatives include those which are not sufficiently stable, those which are stable but deficient in the bioactivity and exhibit no vitamin C activity in vivo, and those which are stable and can have a vitamin C activity in vivo but have bad cutaneous absorption and are not suitable for external application through the skin differently from the agent for preventing and treating skin diseases according to the present invention.

The ascorbic acid derivatives generally contain as impurities oxalic acid, which is a decomposition product of ascorbic acid, and unreacted ascorbic acid. The oxalic acid has strong cytotoxicity and gives intense irritation on the skin. The ascorbic acid exhibits strong acidity and induces inflammation or irritation on the skin. Therefore, if the ascorbic acid derivatives containing large amounts of the impurities are used on the skin suffering from inflammation, the irritation becomes a problem and cancels the effect of the ascorbic acid derivatives. Especially when an ascorbic acid derivative containing oxalic acid in an amount of more than 3% and ascorbic acid in an amount of more than 0.3% is applied to the oversensitive skin such as skin with atopic skin diseases, various side effects such as stinging, irritating, chapping and rubric eczema are brought about on the skin. Thes[0085] sid[0085] effect ar[0085] als foun[0084] i[008e] th[0085] application of a crude ascorbic acid derivative product having a high content of unreacted ascorbic acid as well as a high content of oxalic acid. The reason is presumably that the ascorbic acid is oxidatively decomposed and partly converted into oxalic acid through dehydroascorbic acid with the passage of time.

The present invention has been made in view of the background, and it is an object of the present invention to provide an agent for effectively preventing and/or treating skin diseases and a composition containing the agent. The present invention has been accomplished by selecting preferably a stably durable high-purity L-ascorbic acid derivative having high skin permeability and ascorbic acid activity (sometimes simply referred to as an "active and durable ascorbic acid derivative" hereinafter) from a large number of ascorbic acid derivatives.

DISCLOSURE OF THE INVENTION

The agent for preventing and treating skin diseases according to the present invention comprises as an active ingredient an ascorbic acid derivative which is a compound represented by the following formula (1) or a-salt thereof and which per se exhibits no anti-oxidation activity but is capable of transforming in vivo into a compound having an anti-oxidation activity;

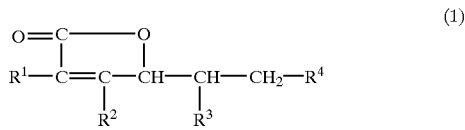

wherein $R^1$ represents a group capable of bonding to the carbon at the 2-position of the ascorbic acid skeleton through an ether or ester bond and transformable in vivo into a hydroxyl group, and $R^2$ to $R^4$ may be the same or different and each represents a hydroxyl group or a group derived therefrom.

As the salt of the compound represented by the formula (1) may be exemplified a sodium, potassium, magnesium or zinc salt thereof, and may be exemplified particularly preferably a sodium, potassium or zinc salt thereof.

The ascorbic acid derivative mentioned above is preferably L-ascorbic acid-2-phosphate, L-ascorbic acid-2-glycoside, 6-alkylcarbonyloxy-L-ascorbic acid-2-phosphate, 6-alkylcarbonyloxy-L-ascorbic acid-2-glycoside, or a sodium, potassium, magnesium or zinc salt thereof, and is particularly preferably sodium L-ascorbic acid-2-phosphate. The ascorbic acid derivatives mentioned above may be used in combination of two or more kinds.

The ascorbic acid derivative mentioned above is preferably a high-purity ascorbic acid derivative containing as impurities oxalic acid in an amount of not more than 3.0% and ascorbic acid in an amount of not more than 0.3%. It is also preferable that the ascorbic acid derivative mentioned above has high skin permeability and is stably durable.

The agent for preventing and treating skin diseases preferably further comprises as an active ingredient a radical scavenging agent other than ascorbic acid and a derivative thereof.

The agent for preventing and treating skin diseases is preferably used, first, as an agent for preventing and treating comedos. The agent for preventing and treating comedos is preferably an agent for preventing and treating comedo vestiges. Further, the agent for preventing and treating comedos is preferably an agent for preventing and treating pigmentation as the comedo vestige, and the comedo vestige is preferably topical cutaneous impression.

The agent for preventing and treating skin diseases is also preferably used as an agent for treating atopic skin diseases. The agent for treating atopic skin diseases is preferably an agent for treating pigmentation as an atopic skin disease vestige, and is also preferably an agent for treating cutaneous impression as an atopic skin disease vestige.

The agent for preventing and treating skin diseases is also preferably used as a wound healing agent. The wound healing agent is preferably an agent for healing pigmentation as a wound scar, is also preferably an agent for healing keloid as a wound scar, and is also preferably an agent for healing wounds caused by scald or burn.

In the agent for preventing and treating skin diseases, the amount of the ascorbic acid derivative is preferably in the range of 0.09 to 1 mol/L in terms of an ascorbic acid unit.

In the agent for preventing and treating skin diseases, it is preferable that the ascorbic acid derivative has been blended by means of phospholipid emulsification or liposome microencapsulation.

BEST MODE FOR CARRYING OUT THE INVENTION

The agent for preventing and treating skin diseases according to the present invention is intended for the whole range of skin diseases, but the agent effectively acts on particularly comedos, atopic skin diseases, wounds and the like.

That is to say, the agent for preventing and treating skin diseases according to the present invention can be favorably used as an agent for preventing and treating comedos, an agent for treating atopic skin diseases, a wound healing agent or the like.

The ascorbic acid derivative contained as an active ingredient in the agent for preventing and treating skin diseases according to the present invention is a compound having an ascorbic acid skeleton and represented by the aforesaid formula (1) (wherein $R^1$ represents a group capable of bonding to the carbon at the 2-position of the ascorbic acid skeleton through an ether or ester bond and transformable in vivo into a hydroxyl group, and $R^2$ to $R^4$ may be the same or different and each represents a hydroxyl group or a group derived therefrom) or a salt thereof.

The ascorbic acid derivative represented by the formula (1), which is employable in the present invention, has a group $R^1$ capable of bonding to the carbon at the 2-position of the ascorbic acid skeleton through an ether or ester bond, so that the ascorbic acid derivative itself exhibits no anti-oxidation activity peculiar to ascorbic acid and is stable because it is hardly oxidatively decomposed. The ascorbic acid derivative is presumed to be transformed in vivo into a compound of a structure having an ascorbic acid activity in vivo, for example, when absorbed through the skin, and as a result, the thus transformed compound exhibits in vivo an anti-oxidation activity peculiar to ascorbic acid and favorably acts on skin diseases.

In the present invention, the formula (1) maybe replaced with a tautomer of the formula (1) or the like, which is considered to substantially have an ascorbic acid skeleton.

With respect to $R^1$, the ether bond is preferably a C—O—C bond of an acetal group or a ketal group, and is, for example, an ether bond with an aliphatic alcohol of 2 to 14 carbon atoms such as ethyl alcohol, isopropyl alcohol or octyl alcohol, or an ether bond with sugar such as glucose, fructose, sucrose, lactose or trehalose. With respect to $R^1$, the ester bond is, for example, an ester bond with an inorganic acid, e.g., a carbonic acid group or a phosphoric acid group such as a monophosphoric acid group (sometimes simply referred to as a "phosphoric acid group"), a pyrophosphoric acid group, a triphosphoric acid group or a polyphosphoric acid group, or an ester bond with an aliphatic or aromatic organic acid such as palmitic acid, stearic acid or benzoic acid. Preferred examples include a monophosphoric acid group, a pyrophosphoric acid group, a triphosphoric acid group, a polyphosphoric acid group and a glycosyl group.

$R^2$ to $R^4$ are each a hydroxyl group or a group derived from a hydroxyl group such as a phosphoric acid group, a glycosyl group, an acyloxy group, an alkyloxy group, an alkenyloxy group or a phenoxy group which may have a substituent.

$R^2$ is preferably a hydroxyl group.

$R^3$ and $R^4$ are each preferably a hydroxyl group or an acyloxy group. The acyloxy group is preferably an acyloxy group derived from a long-chain fatty acid (long-chain alkylcarbonyloxy group).

It is preferable that $R^3$ and $R^4$ are each a hydroxyl group or that one of $R^3$ and $R^4$ is a hydroxyl group and the other is an acyloxy group derived from a fatty acid.

Examples of the ascorbic acid derivatives employable in the present invention include L-ascorbic acid-2-phosphate and salts thereof, L-ascorbic acid-2-glycoside, 6-alkylcarbonyloxy-L-ascorbic acid-2-phosphate and salts thereof, 6-alkylcarbonyloxy-L-ascorbic acid-2-glycoside and salts thereof, and 2,3,5,6-tetraalkylcarbonyloxyascorbic acid.

In the L-ascorbic acid-2-phosphate and salts thereof employable in the present invention, the phosphoric acid group at the 2-position is preferably a monophosphoric acid group.

The L-ascorbic acid-2-glycoside employable in the present invention is preferably a glycoside in which glucose is present at the 2-position, such as L-ascorbic acid-2-glucoside (2-O-α-D-glucopyranosil-L-ascorbic acid). Examples thereof include L-ascorbic acid-2-glucoside and salts thereof, 5,6-O-alkylidene-L-ascorbic acid-2-glucoside, and 5,6-O-benzylidene-L-ascorbic acid-2-glucoside and salts thereof.

In the 6-alkylcarbonyloxy-L-ascorbic acid-2-phosphate and salts thereof, $R^4$ in the formula (1) is —OC(O)R wherein R is preferably an alkyl group of 4 to 21 carbon atoms.

Specific examples thereof include 6-butylyloxy-L-ascorbic acid-2-phosphate, 6-palmitoyloxy-L-ascorbic acid-2-phosphate, 6-stearoyloxy-L-ascorbic acid-2-phosphate, 6-oreoyloxy-L-ascorbic acid-2-phosphate, 6-myristoyloxy-L-ascorbic acid-2-phosphate, 6-dodecanoyloxy-L-ascorbic acid-2-phosphate, 6-tetradecanoyloxy-L-ascorbic acid-2-phosphate, 6-(cis-9-octadecenoyloxy)-L-ascorbic acid-2-phosphate, 6-linoloyloxy-L-ascorbic acid-2-phosphate, 6-linolenoyloxy-L-ascorbic acid-2-phosphate, 6-arachidonoylbxy-L-ascorbic acid-2-phosphate, 5,6-O-benzylidene-L-ascorbic acid-2-phosphate, and salts thereof.

In the 6-alkylcarbonyloxy-L-ascorbic acid-2-glucoside and salts thereof, $R^4$ in the formula (1) is —OC(O)R wherein R is preferably an alkyl group of 4 to 21 carbon atoms.

Specific examples thereof include 6-butylyloxy-L-ascorbic acid-2-glucoside, 6-palmitoyloxy-L-ascorbic acid-2-glucoside, 6-stearoyloxy-L-ascorbic acid-2-glucoside, 6-oreoyloxy-L-ascorbic acid-2-glucoside, 6-myristoyloxy-L-ascorbic acid-2-glucoside, 6-dodecanoyloxy-L-ascorbic acid-2-glucoside, 6-tetradecanoyloxy-L-ascorbic acid-2-glucoside, 6-(cis- 9-octadecenoyloxy)-L-ascorbic acid-2-glucoside, 6-linoloyloxy-L-ascorbic acid-2-glucoside, 6-linolenoyloxy-L-ascorbic acid-2-glucoside, 6-arachidonoyloxy-L-ascorbic acid-2-glucoside, 5,6-O-benzylidene-L-ascorbic acid-2-glucoside, and salts thereof.

A specific example of the 2,3,5,6-tetraalkylcarbonyloxyascorbic acid is 2,3,5,6-O-tetra-2-hexyldecanoyl-L-ascorbic acid.

Examples of the salts employable as the ascorbic acid derivatives include salts with cations of ammonium, sodium, potassium, magnesium, calcium, strontium, barium, aluminum, iron, zinc, bismuth and organic amines. A salt with at least one of these cations is preferable. More preferable is a sodium, potassium, magnesium or zinc salt, still more preferable is a sodium, potassium or zinc salt, and particularly preferable is a sodium salt. The above-mentioned compounds in the form of water or crystal water addition products may also be used as the ascorbic acid derivatives.

Of the ascorbic acid derivatives which can be used in the present invention, those exerting an excellent effect are a sodium salt, a potassium salt and a zinc salt of L-ascorbic acid-2-monophosphate, and L-ascorbic acid-2-glucoside. In particular, the sodium salt of L-ascorbic acid-2- monophosphate is preferable. The magnesium salt and the calcium salt of L-ascorbic acid-2-monophosphate have an effect but the effect is inferior to that of the sodium salt. This is considered to be ascribable to their cutaneous absorptivity inferior to that of the sodium salt.

The L-ascorbic acid derivative usually contains as impurities oxalic acid, which is a decomposition product of ascorbic acid, and unreacted ascorbic acid. The oxalic acid has strong cytotoxicity and the ascorbic acid exhibits strong acidity, so that they induce irritation on the skin. Especially when the skin suffers from inflammation of comedos or the like, the irritation is found to cause a problem of giving bad effects on the treatment of comedos. In the present invention, therefore, it is preferable to use a high-purity ascorbic acid derivative containing not more than 3.0% (by weight) of oxalic acid or not more than 0.3% (by weight) of ascorbic acid as impurities of the ascorbic acid derivative that is an active ingredient, and it is particularly preferable to use a high-purity ascorbic acid derivative containing not more than 3.0% (by weight) of oxalic acid and not more than 0.3% (by weight) of ascorbic acid as impurities of the ascorbic acid derivative. By the use of such a high-purity ascorbic acid derivative, the above-mentioned problem can be solved.

In the present invention, a stably durable L-ascorbic acid derivative having high skin permeability and ascorbic acid activity may be preferably used. This active and durable ascorbic acid derivative means an ascorbic acid derivative which exhibits "+" both in the following tests (a) and (b).

(a) Test of Skin Permeability and Ascorbic Acid Activity:

In the following test, those absorbed into skin are evaluated as "+" and those not absorbed as "−".

The dorsum skin with corium of a 4- or 5-week-old hairless mouse was abraded and the skin abraded from the back of the hairless mouse was fixed in an H-type transverse diffusion cell. Then, 2 ml of DALBECCO PBS(−) was charged into the receiver-side cell and 2 ml of a specimen was charged into the donor-side cell. After incubation at 37° C. for from 30 to 120 minutes, 200 μl was sampled from the donor-side cell and 200 μl of DALBECCO PBS(−) was replenished. An ascorbic acid amount of the solution sampled was analyzed by the HPLC method described later in the Examples. When an ascorbic acid transmitted through the skin was detected and identified, the evaluation was "+" and when an ascorbic acid was not detected and identified, the evaluation was "−". When a peak on the order of a trace was confirmed, the evaluation was "±".

(b) Test of Activity Duration:

In the following test, those sustained in the stability were evaluated as "+" and those not sustained as "−".

An ascorbic acid derivative was dissolved in water to have a concentration of 0.5% (in the case of an oil-soluble SF-621 US material, it was emulsion-dispersed in an ordinary manner by adding 2% of a surfactant Tween 80 (trademark)) and stored at 40° C. for one month. Then the residual amount of the derivative was measured by the HPLC method described later in the Examples. When the residual ratio was 90% or more, the evaluation was "+" and when it was less than 90%, the evaluation was "−".

In the present invention, the radical scavenging agent other than an ascorbic acid or a derivative thereof, which can be used in combination with the L-ascorbic acid derivative, is appropriately selected from dl-α-tocopherol, dl-α-tocopherol acetic acid ester, sodium dl-α-tocopherol phosphate or a potassium salt, a magnesium salt and a calcium salt thereof, dl-α-tocopherol acetic acid ester, vitamin E and derivatives thereof such as vitamin E nicotinate, an antioxidant such as ubiquinone, erythorbic acid, tea extract, polyphenols and ethoxychin, a cartinoid such as astaxanthin, an organic acid such as citric acid, phosphoric acid, metaphosphoric acid, glycine and cysteine, and a polyphenol such as catechin, and an alkali metal or alkaline earth metal salt thereof such as sodium, potassium, magnesium and calcium. Of these, a combination use with one or more substances selected from carotene, astaxanthin, lutein, dl-α-tocopherol acetic acid ester, a-tocopherol, SOD, glutathione, dibutylhydroxyltoluene, butylhydroxyanisole, propyl gallate, catechines, and an alkali metal or alkaline earth metal salt thereof such as sodium, potassium, magnesium or calcium, gives a high effect on the action.

A composition containing the agent for preventing and treating skin diseases according to the present invention is increased in the effect of preventing and treating comedos by blending the agent in a composition or a preparation in such an amount that a concentration of the ascorbic acid derivative in the composition or the preparation is in the range of 0.09 to 1 mol/L in terms of an ascorbic acid unit or by using liposome capsules for the purpose of imparting high skin permeability.

If desired, it is possible that the active ingredient employable in the present invention is coated with a coating agent such as gelatin or fats and oils or subsumed with microcapsule or dextrin and the thus treated active ingredient is added to a preparation. As the liposome microcapsule for the present invention, any of known liposome preparations produced by conventional processes and liposomes prepared by known processes can be favorably employed. Specifically, liposomes described in, for example, Japanese Patent Laid-Open Publications No. 316079/1995, No. 151334/1996 and No. 278726/1997 can be employed.

The content of the ascorbic acid derivative used as an active ingredient of the agent for preventing and treating skin diseases according to the present invention is in the range of 0.09 to 1 mol/L, preferably 0.1 to 1 mol/L, more preferably 0.1 to 0.3 mol/L, in terms of an ascorbic acid unit, based on the whole composition containing the agent for preventing and treating skin diseases.

When a radical scavenging agent is used in combination, the content of the radical scavenging agent is in the range of 0.001 to 0.1 mol/L, preferably 0.01 to 0.1 mol/L, based on the whole composition containing the agent for preventing and treating skin diseases according to the present invention.

The dose of the agent for preventing and treating skin diseases according to the present invention is properly determined according to the relative gravity or grade of symptom of a patient or the diagnosis by a physician, and is not particularly limited. In general, the dose per day per kg of the weight of a patient is in the range of 0.01 to 1 mmol, preferably about 0.05 to about 0.5 mmol, in terms of the ascorbic acid derivative, independent of the drug shape. In case of an injection of the agent for preventing and treating skin diseases, however, the dose is desired to be in the range of usually 0.001 to 1 mmol, preferably about 0.005 to about 0.05 mmol, because of high absorptivity.

According to the present invention, an agent for preventing and treating skin diseases, which has no side effect as possessed by steroid agents and exerts an excellent effect on the treatment and prevention of skin diseases, can be provided.

When the agent of the present invention is used as an agent for preventing and treating comedos, an effect of eliminating comedo vestiges after the treatment of comedos is exerted. To be noteworthy, this effect is brought out especially when the comedo vestige is pigmentation or topical cutaneous impression.

The agent for preventing and treating skin diseases is also effective for pigmentation or cutaneous impression as an atopic skin disease vestige, such pigmentation or cutaneous impression being frequently brought about after conventional treatment of the atopic skin diseases. By the use of the agent of the present invention as an agent for treating atopic skin diseases during or after the treatment, the pigmentation or cutaneous impression as an atopic skin disease vestige can be eliminated to recover the normal skin.

Further, the agent for preventing and treating skin diseases also exerts an excellent wound healing effect and is effective for pigmentation or cutaneous impression as a wound scar. That is to say, by the use of the agent of the present invention as a wound healing agent during or after the treatment, the pigmentation or cutaneous impression as a wound scar can be eliminated to recover the normal skin.

The agent for preventing and treating skin diseases according to the present invention may have any shape, and can be used over a wide range, for example, in medicines, quasi-drugs, cosmetics and toiletries. Examples of uses thereof include an agent for external application, a poultice, a patch, an oily ointment, an aqueous ointment, a cream, a cosmetic lotion, a lotion, an emulsion, a face lotion, a pack, a soap, a face wash, an ointment, a hard salve, a liniment, a gel, a plaster, a cataplasm, a spray, a bath preparation, a hair liquid, a hair tonic, a shampoo, a rinse, a hair restorer, a makeup and a body makeup.

In addition to the above-mentioned active ingredients as essential components, other ingredients commonly blended in a preparation, such as a surfactant, an oil, an alcohol, a moisturizer, a thickener, an antiseptic, an antioxidant, a chelating agent, a pH adjuster, a perfume, a dye, an ultraviolet light absorbing/scattering agent, an amino acid and water, may be appropriately blended in the agent for preventing and treating skin diseases according to the present invention. These ingredients can be used in amounts of 0.0001 to 90% by weight based on the agent for preventing and treating skin diseases according to the present invention.

Examples of the surfactant include nonionic surfactants such as lipophilic glycerin monostearate, selfemulsifying glycerin monostearate, polyglycerin monostearate, sorbitan monooleate, polyethylene glycol monostearate, polyoxyethylene sorbitan monooleate, polyoxyethylene cetyl ether, polyoxyethylated sterol, polyoxyethylated lanolin, polyoxyethylated beeswax and polyoxyethylene hydrogenated castor oil, anionic surfactants such as sodium stearyl phosphate, potassium palmitate, sodium cetylsulfate, sodium lauryl phosphate, triethanolamine palmitate, sodium polyoxyethylene lauryl phosphate and sodium N-acylglutamate, cationic surfactants such as stearyldimethylbenzylammonium chloride and stearyltrimethylammonium chloride, and amphoteric surfactants such as alkylaminoethylglycine chloride solution and lecithin.

Examples of the oil include vegetable oils and fats such as castor oil, olive oil, cacao oil, tsubaki oil, coconut oil, Japan wax, jojoba oil, grape seed oil and avocado oil, animal oils and fats such as mink oil and egg yolk oil, waxes such as beeswax, spermaceti, lanolin, carnauba wax and candelilla wax, hydrocarbons such as liquid paraffin, squalane, microcrystalline wax, ceresine wax, paraffin wax and petrolatum, natural and synthetic fatty acids such as lauric acid, myristic acid, stearic acid, oleic acid, isostearic acid and behenic acid, natural and synthetic higher alcohols such as cetanol, stearyl alcohol, hexyldecanol, octyldodecanol and lauryl alcohol, and esters such as isopropyl myristate, isopropyl palmitate, isopropyl adipate, octyldodecyl myristate, octyldodecyl ole ate and cholesterol oleate.

Examples of the moisturizer include polyhydric alcohols such as glycerin, propylene glycol, 1,3-butylene glycol, sorbitol, polyglycerin, polyethylene glycol and dipropylene glycol, NMF ingredients such as amino acid and sodium lactate, and water-soluble polymer substances such as hyaluronic acid, collagen, muco-polysaccharide and chondroitin sulfiuric acid.

Examples of the thickener include natural polymer substances such as sodium alginate, xanthan gum, aluminum silicate, quince seed extract, tragacanth gum and starch, and semisynthetic polymer substances such as methyl cellulose, hydroxyethyl cellulose, carboxymethyl cellulose, soluble starch and cationized cellulose.

Examples of the chelating agent include disodium edetate, ethylenediaminetetraacetate, pyrophosphate, hexametaphosphate, citric acid, tartaric acid and gluconic acid. Examples of the pH conditioner include sodium hydroxide, triethanolamine, citric acid, sodium citrate, boric acid, borax and potassium hydrogenphosphate.

Examples of the ultraviolet absorbing/scattering agent which can be used in combination include p-amino acid type, hydroxybenzophenone type, benzofuran type, salicyclic acid type, coumarin type and azole type organic ultraviolet absorbents, such as 2-hydroxy-4-methoxybenzophenone, octyldimethyl p-aminobenzoate and ethylhexyl p-methoxycinnamate, and this is used in an amount of from 0.001 to 10 mol/L. Furthermore, titanium oxide, kaolin or talc may also be used in combination. Examples of the amino acid include glycine, alanine, valine, leucine, isoleucine, serine, threonine, phenylalanine, tyrosine, tryptophan, cystine, cysteine, methionine, proline, hydroxyproline, aspartic acid, asparagine, glutamic acid, glutamine, histidine, lysine, and derivatives thereof.

The present invention may also be used in combination with 0.001 to 10 mol/L of a whitening cosmetic material commonly used. Examples of the whitening cosmetic materials employable in combination include kojic acid, placenta extract, arbutin, SS arbutin, morusin, ellagic acid and chamomile extract.

An antiinflammatory ingredient or an antiphlogistic ingredient commonly used may be added to the present invention, because when the present invention is used in combination with 0.001 to 10 mol/L of the antiinflammatory ingredient or antiphlogistic ingredient, an antiphlogistic effect on comedos, atopic skin diseases, wounds and the like is accelerated. Examples of the antiphlogistic ingredients which can be added to the present invention include salicylic acid derivative type antiphlogistic, aniline derivative type antiphlogistic, anticonvulsant, pyrazolone derivative type antiphlogistic, indomethacin-based antiphlogistic, mefenamic acid-based antiphlogistic, antihistamines, antiallergic and inflammation-loving enzymatic steroid agent, but the ingredients employable are not particularly limited.

In addition, a bactericide, a chelating agent, a plant extract ingredient and other ingredients commonly used may be added to the agent for preventing and treating skin diseases. Examples of the other ingredients which can be added to the present invention include isopropylmethylphenol, sulfur, dipotassium glycyrrhizinate, resorcin, paraben, diisopropanolamine, cetostearyl alcohol, propylene glycol, methylparaben, propylparaben, isopropyl myristate, sodium hydrogensulfite, tretinoin, clindamycin, erythromycin, benzoyl peroxide, azelaic acid, TRICRONSAN (IRGASAN-DP300), glycyrrhizinic acid or a salt thereof such as a sodium or potassium salt thereof, triethanolamine, cypress extract, hinokitiol, edetate, propylene glycol, perilla extract, rosemary extract, rose extract, chamomile extract, melissa extract, sage extract, glycyrrhiza extract, jojoba extract, N-acyl-L-glutamic acid or a salt thereof such as a sodium salt thereof, cetanol, mukurossi extract, and squalane such as phytosqualane As the additives which can be added to the agent for preventing and treating skin diseases according to the present invention, those described in the standards of cosmetic additives such as Keshohin Genryo Kijun-Gai Seibun Kikaku, Tsuiho (*Standards of Ingredients other than those listed in JSCI, Supplement*), issued by Yakuji Nippo Ltd. (1993) may be added for ordinary purposes.

Furthermore, pharmaceutical ingredients described in the standards of pharmaceutical ingredients such as *Japanese Pharmacopoeia*, 13th rev., issued by Hirokawa Shoten (1996), Irvoaku. Nippon Iyakuhin Shu (*Medicinal Preparation, List of Japanese Drugs*) (October, 1997), compiled by Nippon Iyaku Joho Center, issued by Yakugyo Jiho Sha, and Ippan Yaku, Nippon Ivakuhin Shu (*General Medicines, List of Japanese Drugs*) (1998–99). 11th edition (issued on Nov. 10. 1997). pp. 1–1100, compiled by Nippon Iyaku Joho Centor, issued by Yakugyo Jiho Sha may be added for ordinary purposes. Of the pharmaceutical ingredients, the following ingredients registered as drugs for external application are preferably used in combination. Specific examples of the ingredient include acrinol, alkylpolyaminoethylglycine, isopropanol, ethanol, benzalkonium chloride, benzethonium chloride, hydrochloric acid addition phenol, hydrogen peroxide solution, potassium permanganate, chlorhexidine gluconate, cresol soap, sodium hypochloride, sodium thiosulfate geraniol-denatured alcohol, thimerosal, phenol, BRONOPOL, povidone-iodine, formalin, mercurochrome, iodine, tincture of iodine, iodoform, resorcin, aluminum chlorohydroxyallantoinate, zinc oxide, white petrolatum, pigskin, erythromycin, oxytetracycline hydrochloride, oxytetracycline hydrochloride polymyxin B sulfate, gramicidin S hydrochloride streptomycin sulfate, tetracycline hydrochloride, dimethylchlorotetracycline hydrochloride, Glamycortisone, CHROMY P, chloramphenicol, sulfadiazine, silver sulfadiazine, sulfisomidine, tetracycline, nadifloxacin, bacitracin fradiomycin sulfate, sodium fusidate, kanamycin sulfate, gentamycin sulfate, colistin sulfate, fradiomycin sulfate, fradiomycin sulfate, fradiomycin trypsin sulfate, polymyxin B sulfate, acrinol tincture oil, azulene, ethyl aminobenzoate, amcinonide, aluminum chlorohydroxyallantoinate, aqueous ammonia, indomethacin, ufenamate, Eksalb, isothipendyl hydrochloride, oxytetracyclinehydrocortisone hydrochloride, tetracycline hydrochloride hydrocortisone acetate, EURICH, antiphlogistic analgesic compound for external application, calamine, carbazochrom alkylpolyaminoethylglycine hydrochloride, camphor, prednisolone acetate valerate, diflucortolone valerate, dexamethasone valerate, betamethasone valerate, betamethasone valerate gentamycin sulfate, Strong Restamin Cortisone, glycyrrhezinic acid, crotamiton, ketoprofen, KENACORT A, KENACORT AG, diflorasone acetate, dexamethasone acetate, lead acetate, hydrocortisone acetate, methyl prednisolone acetate, methyl salicylate, zinc chloride, S UNKO, diphenhydramine, DIFLUPREDONATE, betamethasone dipropionate, bismuth subgallate, calcium hydroxide, suprofen, marronier seed extract, defatted soybean dry distilled tar, defatted soybean dry distillated tar diphenhydramine, tannic acid, dexamethasone, dexamethasone defatted soybean dry distilled tar, capsicum tincture, tocopherol vitamin A oil, triamcinolone acetonide, halcinonide, vitamin A, hydrocortisone crotamiton, FUFUMETHASONE pivalate, PYRIDORETIN, pyroxicam, phenol zinc white liniment, felbinac, PTESONIDO, bufexamac, momethasone furancarboxylic acid, fluocinonide, fluocinolone acetonide, fludroxycortide, flurbiprofen, prednisolone, alclometasone propionate, clobetasol propionate, dexamethasone propionate, deprodone propionate, BECROMETHASONE propionate, betamethasone, heparin analogs, bendazac, Mobilat, lauryl diphenhydramine sulfate, CLOBETASONE butyrate, hydrocortisone butyrate, betamethasone butyrate propionate, hydrocortisone butyrate propionate, potassium aluminum sulfate, fradiomycin ammonium sulfate betamethasone valerate, fradiomycin ammonium sulfate fluocinolone acetonide, fradiomycin ammonium sulfate prednisolone, sulfur, undecylenic acid, zinc undecylenate, undecylenic acid zinc undecylenate, undecylenic acid salicylic acid, AMOROLFIN hydrochloride, croconazole hydrochlorite, terbinafine hydrochloride, neticonazole hydrochloride, butenafine hydrochloride, clotrimazole, ketoconazole, ciclopirox olamine salicylate, siccanin, isoconazole nitrate, ECONAZOLE nitrate, oxyconazole nitrate, sulconazole nitrate, STARCH MERCURY, thioconazole, trichomycin, TRICYCLATE, tolnaftate, trinaphthate chlorhexidine hydrochloride, nystatin, variotin, BIHONAZOLE, phenyl iodoundecynoate, miconazole, wood tar, lanoconazole, sulfur camphor, potash soap, cantharis, glycerinated potash, acetic acid, salicyclic acid, silver nitrate, urea, carpronium hydrochloride, alprostadil, diaphenylsulfone, purified saccharose povidone-iodine, TACALSITOL, tritinoin tocoferil, bucladesine sodium, heparin sodium, methoxsalen, Meladinine, ibuprofen, ibuprofen picol, young bovine blood extract and iodine. Such an ingredient may be added and used in combination in an amount of from 0.0001 to 50 wt %.

In the case where the comedo preventing and treating agent of the present invention is used as a general dermal composition for external application, a cosmetic material or a quasi-drug (non-official medical product), the active ingredients each is blended in such an amount as described below, however, the present invention is by no means limited thereto.

Although it varies depending on the shape of the preparation and the molecular weight of the ascorbic acid derivative, an ascorbic acid derivative is added in an amount of approximately from 0.4 to 12.0 wt % and a radical scavenging agent is added in an amount of from 0.05 to 10 wt %. In the case of powder, a preparation having a concentration of from 4 to 100% may be produced and this is preferably used after appropriately diluting it to from 4 to 12%.

Preferred use methods of the agent for preventing and treating skin diseases according to the present invention are described below:

(1) a composition for preventing and treating skin diseases, which contains an active and durable ascorbic acid derivative in an amount of 0.09 to 1 mol/L, preferably 0.1 to 1 mol/L, more preferably 0.1 to 0.3 mol/L, based on the whole composition for preventing and treating skin diseases, (2) an agent for preventing and treating skin diseases, which contains a radical scavenging agent other than ascorbic acid or a derivative thereof in an amount of 0.001 to 0.1 mol/L based on the whole composition for preventing and treating skin diseases, and (3) an agent for preventing and treating skin diseases, which is a dermal agent for external application in a form selected from the group consisting of an oily ointment, an aqueous ointment, a cream, a cosmetic lotion, a lotion, an emulsion, a face lotion, a pack, a soap, a face wash, a makeup and a body makeup.

According to the present invention, an agent for preventing and treating skin diseases, which has no side effect as possessed by steroid hormone agents and exerts an excellent effect of preventing and treating skin diseases such as comedos, atopic skin diseases and wounds, can be provided.

EXAMPLE

The present invention is described in greater detail below by referring to the Examples, however, the present invention should not be construed as being limited thereto.

Agents for preventing and treating skin diseases were prepared according to the following formulations in a usual manner. The blended amount is shown by the unit of % by weight. The "balance" means a remaining amount necessary for making 100%.

Example 1

Solution

| (Ingredients Blended) | (Amount Blended) |
| --- | --- |
| 1. Sorbitol | 4.0 |
| 2. Dipropylene glycol | 6.0 |
| 3. PEG1500 | 5.0 |
| 4. POE(20) oleyl alcohol ether | 0.5 |
| 5. Methyl cellulose | 0.2 |
| 6. Citric acid | 0.01 |
| 7. Sodium hydroxide | trace amount (for adjusting the pH to 7.5) |
| 8. Sodium L-ascorbic acid-2-phosphate | 5.0 |
| 9. Sodium dl-α-tocopherolphosphate | 0.5 |
| 10. Purified water | balance |

Example 2

Solution

| (Ingredients Blended) | (Amount Blended) |
| --- | --- |
| 1. Sorbitol | 4.0 |
| 2. Dipropylene glycol | 6.0 |
| 3. PEG1500 | 5.0 |
| 4. POE(20) oleyl alcohol ether | 0.5 |
| 5. Methyl cellulose | 0.2 |
| 6. Citric acid | 0.01 |
| 7. Sodium hydroxide | trace amount (for adjusting the pH to 7.5) |
| 8. Sodium L-ascorbic acid-2-phosphate | 7.0 |
| 9. Purified water | balance |

Example 3

Solution

| (Ingredients Blended) | (Amount Blended) |
| --- | --- |
| 1. Sorbitol | 4.0 |
| 2. Dipropylene glycol | 6.0 |
| 3. PEG1500 | 5.0 |

-continued

| (Ingredients Blended) | (Amount Blended) |
| --- | --- |
| 4. POE(20) oleyl alcohol ether | 0.5 |
| 5. Methyl cellulose | 0.2 |
| 6. Citric acid | 0.01 |
| 7. Sodium hydroxide | trace amount (for adjusting the pH to 7.5) |
| 8. Sodium L-ascorbic acid-2-phosphate | 7.5 |
| 9. Purified water | balance |

Example 4

Solution

| (Ingredients Blended) | (Amount Blended) |
| --- | --- |
| 1. Sorbitol | 3.8 |
| 2. Dipropylene glycol | 5.5 |
| 3. PEG1500 | 5.0 |
| 4. POE(20) oleyl alcohol ether | 0.5 |
| 5. Methyl cellulose | 0.2 |
| 6. Citric acid | 0.01 |
| 7. Potassium hydroxide | trace amount (for adjusting the pH to 7.5) |
| 8. Potassium L-ascorbic acid-2-phosphate | 6.5 |
| 9. Potassium dl-α-tocopherolphosphate | 0.7 |
| 10. Purified water | balance |

Example 5

Emulsion

| (Ingredients Blended) | (Amount Blended) |
| --- | --- |
| 1. Glyceryl ether | 1.5 |
| 2. Polyoxyethylene (20) hydrogenated castor oil | 1.5 |
| 3. Sorbitan monostearate | 1.0 |
| 4. Squalane | 7.5 |
| 5. Dipropylene glycol | 5.0 |
| 6. L-Ascorbic acid-2-glycocide | 5.0 |
| 7. GRABLYSIN | 0.2 |
| 8. Purified water | balance |

Example 6

Lotion or Water-soluble Agent for External Application

| (Ingredients Blended) | (Amount Blended) |
| --- | --- |
| 1. Glycerin monostearate | 1.0 |
| 2. Isopropyl palmitate | 3.0 |
| 3. Lanolin | 1.0 |
| 4. Glycerin | 5.0 |
| 5. Methyl parahydroxybenzoate ester | 0.1 |
| 6. Stearylcolaminoformylpyridinium chloride | 1.5 |
| 7. Zinc L-ascorbic acid-2-phosphate | 5.0 |
| 8. Glycyrrhiza nanking extract | 0.1 |
| 9. Purified water | balance |

Example 7

Ointment

| (Ingredients Blended) | (Amount Blended) |
|---|---|
| 1. White petrolatum | 40.0 |
| 2. Cetanol | 18.0 |
| 3. Sorbitan sesquioleate | 5.0 |
| 4. Lauromacrogol | 0.5 |
| 5. Ethyl paraoxybenzoate | 0.1 |
| 6. Butyl paraoxybenzoate | 0.1 |
| 7. Potassium L-ascorbic acid-2-phosphate | 10.0 |
| 8. Maackia extract | 1.0 |
| 9. Purified water | balance |

Example 8

Cream

| (Ingredients Blended) | (Amount Blended) |
|---|---|
| 1. Propylene glycol | 6.0 |
| 2. Dibutyl phthalate | 19.0 |
| 3. Stearic acid | 5.0 |
| 4. Glycerin monostearate | 5.0 |
| 5. Sorbitan monostearate | 12.0 |
| 6. Polyethylenesorbitan monostearate | 38.0 |
| 7. Methylparaben | 0.06 |
| 8. Propylparaben | 0.03 |
| 9. Sodium edetate | 0.03 |
| 10. Sodium 6-palmitoyloxy-L-ascorbic acid-2-phosphate | 7.0 |
| 11. BESTITOL | 0.05 |
| 12. Purified water | balance |

Example 9

Liposome Preparation

Using a COSMESOME (trademark) series produced by Q.P. Corp., a liposome preparation having the following composition was produced. In the blended components, the yolk lecithin PL-100P produced by Q.P. Corp. contained components of 82% of phosphatidylcholine, 15% of phosphatidylethanolamine, 1% of other phospholipids and 1% of sterols.

| (Ingredients Blended) | (Amount Blended) |
|---|---|
| 1. Yolk lecithin PL-100P produced by Q.P. Corp. | 1.0 |
| 2. Sodium L-ascorbic acid-2-phosphate | 4.0 |
| 3. Phenoxy ethanol | 0.8 |
| 4. Purified water | balance |

Example 10

Ointment

| (Ingredients Blended) | (Amount Blended) |
|---|---|
| 1. White petrolatum | 25.0 |
| 2. Stearyl alcohol | 20.0 |
| 3. Propylene glycol | 12.0 |
| 4. Polyoxyethylene halogenated castor oil 60 | 4.0 |
| 5. Glycerin monostearate | 1.0 |
| 6. Methyl paraoxybenzoate | 0.1 |
| 7. Propyl paraoxybenzoate | 0.1 |
| 8. Sodium L-ascorbic acid-2-phosphate | 1.0 |
| 9. Magnesium L-ascorbic acid-2-phosphate | 1.0 |
| 10. Sodium 6-palmitoyloxy-L-ascorbic acid-2-phosphate | 1.0 |
| 11. Sodium 6-stearoyloxy-L-ascorbic acid-2-phosphate | 1.0 |
| 12. Purified water | balance |

Example 11

Bath Preparation

| (Ingredients Blended) | (Amount Blended) |
|---|---|
| 1. Sodium sulfate | 45.5 |
| 2. Sodium hydrogencarbonate | balance |
| 3. L-Ascorbic acid-2-glucoside | 10.0 |
| 4. Maackia extract | 5.0 |
| 5. Mentol | 0.3 |
| 6. Perfume, Dye | 0.25 |

Test Example 1-1

Comedo Treating Effect

160 Subjects as the patient suffering from comedos were grouped into segments consisting of 20 subjects and a cosmetic solution or the like according to the following Formulation Examples was continuously applied to their face twice per day (after face washing every morning and after having a bath every evening). After two months, the effect on the comedo treatment was judged. The judgment was made by 6-stage rating, namely, very remarkably effective (3 points), remarkably effective (2 points), effective (1 point), no change (0 point), deteriorated (−1 point) and extremely deteriorated (−2 points). An average point of 20 subjects in respective test segments was calculated and the judgement results obtained are shown in Table 1. Skin irritation was also examined.

Furthermore, after 6 months, the treatment effect of comedo vestiges was judged. The judgement was made by 4-stage rating, namely, very remarkably effective (3 points), remarkably effective (2-points), effective (1 point) and no change (0-point). An average point of 20 subjects in respective test segments was calculated and the judgement results obtained are shown in Table 1.

Test Example 1-2

Effect of Treating Atopic Skin Disease

80 Subjects as a patient suffering from atopic skin disease were grouped into segments consisting of 20 subjects and a cosmetic solution or the like according to the following formulation was continuously applied to face twice per day (after face washing every morning and after having a bath every evening). After two months, the therapeutic effect on atopic skin disease was judged. The judgment was made by 6-stage rating, namely, very remarkably effective (3 points), remarkably effective (2 points), effective (1 point), no change (0 point), deteriorated (−1 point) and extremely deteriorated (−2 points). An average point of 10 subjects in respective test segments was calculated and the judgement results obtained are shown in Table 1. Skin irritation was also examined.

Furthermore, after 10 months, the therapeutic effect on atopic skin disease vestiges was judged. The judgement was made by 4-stage rating, namely, very remarkably effective (3 points), remarkably effective (2 points), effective (1 point) and no change (0 point). An average point of 20 subjects in respective test segments was calculated and the judgement results obtained are shown in Table 1.

Test Example 1-3

Wound Healing Effect

80 Subjects as a patient suffering from a wound including a scald were grouped into segments consisting of 10 subjects and a cosmetic solution according to the following formulation was continuously applied to the face twice per day (after face washing every morning and after having a bath every evening). After two months, the wound healing effect was judged. The judgment was done according to the 6-stage rating, namely, very remarkably effective (3 points), remarkably effective (2 points), effective (1 point), no change (0 point), deteriorated (−1 point) and extremely deteriorated (−2 points). An average point of 10 subjects in respective test segments was calculated and the judgement results obtained are shown in Table 1. Skin irritation was also examined.

Furthermore, after 10 months, the therapeutic effect on wound scars was judged. The judgement was done according to 4-stage rating, namely, very remarkably effective (3 points), remarkably effective (2 points), effective (1 point) and no change (0 point). An average point of 20 subjects in respective test segments was calculated and the judgement results obtained are shown in Table 1.

Formulation Example 1

Cosmetic Solution

The same cosmetic solution as in Example 1 was used.

Formulation Example 2

Cosmetic Solution

The same cosmetic solution as in Example 2 was used.

Formulation Example 3

Cosmetic Solution

| (Ingredients Blended) | (Amount Blended) |
|---|---|
| 1. Sorbitol | 4.0 |
| 2. Dipropylene glycol | 6.0 |
| 3. PEG1500 | 5.0 |
| 4. POE(20) oleyl alcohol ether | 0.5 |
| 5. Methyl cellulose | 0.2 |

-continued

| (Ingredients Blended) | (Amount Blended) |
|---|---|
| 6. Citric acid | 0.01 |
| 7. Sodium hydroxide | trace amount (for adjusting the pH to 7.5) |
| 8. Sodium L-ascorbic acid-2-phosphate | 5.0 |
| 9. Purified water | balance |

Formulation Example 4

Liposome Preparation

The same liposome preparation as in Example 9 was used.

Formulation Example 5

Solution

| (Ingredients Blended) | (Amount Blended) |
|---|---|
| 1. Sorbitol | 4.0 |
| 2. Dipropylene glycol | 6.0 |
| 3. PEG1500 | 5.0 |
| 4. POE(20) oleyl alcohol ether | 0.5 |
| 5. Methyl cellulose | 0.2 |
| 6. Citric acid | 0.01 |
| 7. Sodium hydroxide | trace amount (for adjusting the pH to 7.5) |
| 8. Magnesium L-ascorbic acid-2-phosphate | 3.0 |
| 9. Purified water | balance |

Formulation Example 6

Solution

| (Ingredients Blended) | (Amount Blended) |
|---|---|
| 1. Sorbitol | 4.0 |
| 2. Dipropylene glycol | 6.0 |
| 3. PEG1500 | 5.0 |
| 4. POE(20) oleyl alcohol ether | 0.5 |
| 5. Methyl cellulose | 0.2 |
| 6. Citric acid | 0.01 |
| 7. Sodium hydroxide | trace amount (for adjusting the pH to 7.5) |
| 8. Benzalkonium chloride | 0.05 |
| 9. Purified water | balance |

Formulation Example 7

Solution

| | |
|---|---|
| 1. Sorbitol | 4.0 |
| 2. Dipropylene glycol | 6.0 |
| 3. PEG1500 | 5.0 |
| 4. POE(20) oleyl alcohol ether | 0.5 |
| 5. Methyl cellulose | 0.2 |
| 6. Citric acid | 0.01 |
| 7. Sodium hydroxide | trace amount (for adjusting the pH to 7.5) |
| 8. Sodium glycyrrhizinate | 0.1 |
| 9. Purified water | balance |

Formulation Example 8

Solution

| (Ingredients Blended) | (Amount Blended) |
|---|---|
| 1. Sorbitol | 4.0 |
| 2. Dipropylene glycol | 6.0 |
| 3. PEG1500 | 5.0 |
| 4. POE(20) oleyl alcohol ether | 0.5 |
| 5. Methyl cellulose | 0.2 |
| 6. Citric acid | 0.01 |
| 7. Sodium hydroxide | trace amount (for adjusting the pH to 7.5) |
| 8. Purified water | balance |

Formulation Example 9

Solution

| (Ingredients Blended) | (Amount Blended) |
|---|---|
| 1. Sorbitol | 4.0 |
| 2. Dipropylene glycol | 6.0 |
| 3. PEG1500 | 5.0 |
| 4. POE(20) oleyl alcohol ether | 0.5 |
| 5. Methyl cellulose | 0.2 |
| 6. Citric acid | 0.01 |
| 7. Sodium hydroxide | trace amount (for adjusting the pH to 7.5) |
| 8. Sodium L-ascorbic acid-2-phosphate (crude product) | 7.0 |
| 9. Purified water | balance |

TABLE 1

Effect on Skin Disease

| | Test Ex. 1-1 | | Test Ex. 1-2 | | | Test Ex. 1-3 |
|---|---|---|---|---|---|---|
| Skin disease | Comedo | Comedo vestige | Atopic skin disease | Pigmentation or impression after atopic skin | Wound | Pigmentation or impression after wound |
| Form. Ex. 1 | 2.1 | 2.4 | 2.1 | 2.3 | 1.8 | 2.2 |
| Form. Ex. 2 | 2.0 | 1.9 | 2.0 | 2.0 | 2.3 | 1.7 |
| From. Ex. 3 | 1.7 | 1.0 | 1.6 | 1.8 | 1.4 | 1.5 |
| Form. Ex. 4 | 2.2 | 2.3 | 2.2 | 2.3 | 1.9 | 2.0 |
| Form. Ex. 5 | 0.6 | 0.8 | 0.8 | 0.9 | 1.0 | 0.9 |
| Form. Ex. 6 | 0.3 | 0.2 | — | — | — | — |
| Form. Ex. 7 | — | — | 1.0 | 0.3 | 0.9 | 0.4 |
| Form. Ex. 8 | −0.5 | 0.0 | −0.6 | 0.1 | −0.4 | 0 |
| Form. Ex. 9 | 0.5 | 0.8 | 0.9 | 0.8 | 1.0 | 0.8 |

In Test Example 1-1, as seen from Table 1, the agents for preventing and treating skin diseases according to the present invention revealed an effect of treating comedos and an effect of improving comedo vestiges. That is, the agents of the present invention were proved to have an excellent comedo treating effect owing to use of a combination of an active and durable L-ascorbic acid derivative having high skin permeability and a radical scavenging agent other than ascorbic acid and a derivative thereof. In the case of Formulation Example 9, 50% of the subjects suffered from skin irritation due to the preparation, and therefore the use was stopped halfway. The result of Formulation Example 9 is an average of 10 subjects having relatively dull skin irritation. Also in the case of Formulation Example 8, 3 subjects had dull skin irritation. In the case of Formulation Examples 1 to 4, skin irritation was not sensed at all.

In Test Example 1-2, as seen in Table 1, the agents for preventing and treating skin diseases according to the present invention revealed an effect of treating atopic skin diseases and an effect of improving atopic skin disease vestiges. Further, the agents of the present invention were proved to have an excellent atopic skin disease treating effect owing to use of a combination of an L-ascorbic acid derivative and a radical scavenging agent. In the case of Formulation Example 9, 50% of the subjects suffered from skin irritation due to the preparation, and therefore the use was stopped halfway. The result of Comparative Example 4 is an average of the subjects having relatively dull skin irritation. Also in the case of Formulation Example 8, 4 subjects had dull skin irritation. In the case of Formulation Examples 1 to 4, skin irritation was not sensed.

In Test Example 1-3, as seen in Table 1, the agents for preventing and treating skin diseases according to the present invention revealed an effect of healing wounds and an effect of improving wound scars such as pigmentation, keloid and cutaneous impression. That is, the agents of the present invention were proved to have an excellent wound healing effect owing to use of a combination of an L-ascorbic acid derivative and a radical scavenging agent. In the case of Formulation Example 9, 40% of the subjects suffered from skin irritation due to the preparation, and therefore the use was stopped halfway. The result of Formulation Example 9 is an average of the subjects having relatively dull skin irritation. Also in the case of Formulation Example 8, 4 subjects had dull skin irritation. In the case of Formulation Examples 1 to 4, skin irritation was not sensed.

Test Example 2

Determination of Oxalic Acid and Ascorbic Acid

The contents of an oxalic acid and an ascorbic acid in the ascorbic acid derivative used as an active ingredient in the above-described Formulation Examples were determined. The results obtained are shown in Table 2.

(1) The content of an oxalic acid was measured under the following conditions by HPLC according to an absolute calibration curve method.

Detector: ultraviolet absorptiometer (measuring wavelength: 210 nm)

Column: stainless steel tube having an interior size of 4.6 mm and a length of 250 mm, packed with 5-$\mu$m silica gel modified by an octadecyl group Mobile phase: 0.08M acetic acid-sodium acetate buffer solution (pH: 5.0) prepared to contain 2.8 mM of n-hexylamine, 0.1 mM of disodium edetate and 2% of methanol Flow velocity: 0.8 ml/min (2) The content of ascorbic acid was measured under the following conditions by HPLC according to an absolute calibration curve method.

Detector: ultraviolet absorptiometer (measuring wavelength: 254 nm)

Column: stainless steel tube having an interior size of 4.6 mm and a length of 250 mm, packed with 5-μm silica gel modified by an octadecyl group Detector: ultraviolet absorptiometer (measuring wavelength: 254 nm)

Column: stainless steel tube having an interior size of 4.6 mm and a length of 150 mm, packed with 5-μm silica gel modified by an octadecyl group Mobile phase: 0.08M acetic acid-sodium acetate buffer solution (pH: 5.0) prepared to contain 2.8 mM of n-hexylamine, 0.1 mM of disodium edetate and 2% of methanol Flow velocity: 0.8 ml/min

TABLE 2

Amounts of impurities in ascorbic acid derivatives

|  | Oxalic Acid | Ascorbic Acid |
| --- | --- | --- |
| Formulation 1 | 0.01 | 0.00 |
| Formulation 2 | 0.01 | 0.00 |
| Formulation 3 | 0.01 | 0.00 |
| Formulation 4 | 0.02 | 0.01 |
| Formulation 8 | 5.2 | 2.1 |

(content: wt %)

Test Example 3

The ascorbic acid derivatives which can be used in the present invention were examined on the stable duration of high skin permeability and the ascorbic acid activity by performing the following tests for the compounds shown below. The results obtained are shown in Table 3.

Test (A):
Test of Skin Permeability and Ascorbic Acid Activity:

The dorsum skin with corium of a 4- or 5-week-old hairless mouse was abraded and the skin abraded from the back of the hairless mouse was fixed in an H-type transverse diffusion cell. Then, 2 ml of DALBECCO PBS(–) was charged into the receiver-side cell and 2 ml of a specimen was charged into the donor-side cell (in the case of an oil-soluble material, it was emulsion-dispersed in an ordinary manner by adding 2% of a surfactant Tween 80 (trademark)). After incubation at 37° C. for from 30 to 120 minutes, 200 μl was sampled from the donor-side cell and 200 μl of DALBECCO PBS (–) was replenished. An ascorbic acid amount of the solution sampled was analyzed by the HPLC method in the Examples. When an ascorbic acid transmitted through the skin was identified, the evaluation was "+" and when an ascorbic acid was not detected, the evaluation was "–" When a peak on the order of a trace was confirmed, the evaluation was "+".

Test (B):
Test of Durability:

An ascorbic acid derivative was dissolved in water to have a concentration of 0.5% (in the case of an oil-soluble material, it was emulsion-dispersed in an ordinary manner by adding 2% of a surfactant Tween 80 (trademark)) and stored at 40° C. for one month. Then the residual amount of the derivative was measured by the HPLC method. When the residual ratio was 90% or more, the evaluation was "+" and when it was less than 90%, the evaluation was "–".

TABLE 3

| Test Compound | Test (A) | Test (B) |
| --- | --- | --- |
| Ascorbic acid tocopherolphosphate diester | – | + |
| Sodium L-ascorbic acid-2-sulfate | – | + |
| L-Ascorbic acid-2-glucoside | + | + |
| Sodium L-ascorbic acid-2-phosphate | + | + |
| Potassium L-ascorbic acid-2-phosphate | + | + |
| Magnesium L-ascorbic acid-2-phosphate | ± | + |
| Sodium 6-stearoyloxy-L-ascorbic acid-2-phosphate | + | + |
| Sodium 6-palmitoyloxy-L-ascorbic acid-2-phosphate | + | + |
| 6-Stearoyloxy-L-ascorbic acid-2-phosphate | + | + |
| 2-Palmitoyloxy-L-ascorbic acid-2-phosphate | + | + |

What is claimed is:

1. A composition for preventing and treating skin diseases, comprising as an active ingredient an ascorbic acid derivative which is at least one substance selected from the group consisting of 6-alkylcarbonyloxy-L-ascorbic acid-2-phosphate, 6-alkylcarbonyloxy-L-ascorbic acid-2-glycoside, and sodium, potassium and zinc salts thereof and which per se exhibits no anti-oxidation activity but is capable of transforming in vivo into a compound having an anti-oxidation activity.

2. The composition for preventing and treating skin diseases as claimed in claim 1, wherein the ascorbic acid derivative is sodium 6-alkylcarbonyloxy-L-ascorbic acid-2-phosphate.

3. The composition for preventing and treating skin diseases as claimed in claim 1, wherein the ascorbic acid derivative is a high-purity ascorbic acid derivative containing as impurities oxalic acid in an amount of not more than 3.0% and ascorbic acid in an amount of not more than 0.3%.

4. The composition for preventing and treating skin diseases as claimed in claim 2, wherein the ascorbic acid derivative is a high-purity ascorbic acid derivative containing as impurities oxalic acid in an amount of not more than 3.0% and ascorbic acid in an amount of not more than 0.3%.

5. The composition for preventing and treating skin diseases as claimed in claim 1, wherein the ascorbic acid derivative has high skin permeability and is stably durable.

6. The composition for preventing and treating skin diseases as claimed in claim 2, wherein the ascorbic acid derivative has high skin permeability and is stably durable.

7. The composition for preventing and treating skin diseases as claimed in claim 1, which further comprises as an active ingredient a radical scavenging agent other than ascorbic acid and a derivative thereof.

8. The composition for preventing and treating skin diseases as claimed in claim 2, which further comprises as an active ingredient a radical scavenging agent other than ascorbic acid and a derivative thereof.

9. The composition for preventing and treating skin diseases as claimed in claim 7, which is an agent for preventing and treating comedos.

10. The composition for preventing and treating skin diseases as claimed in claim 8, which is an agent for preventing and treating comedos.

11. The composition for preventing and treating skin diseases as claimed in claim 9, wherein the agent for preventing and treating comedos is an agent for preventing and treating comedo vestiges.

12. The composition for preventing and treating skin diseases as claimed in claim 10, wherein the agent for preventing and treating comedos is an agent for preventing and treating comedo vestiges.

13. The composition for preventing and treating skin diseases as claimed in claim 11, wherein the agent for preventing and treating comedos is an agent for preventing and treating pigmentation as the comedo vestige.

14. The composition for preventing and treating skin diseases as claimed in claim 12, wherein the agent for preventing and treating comedos is an agent for preventing and treating pigmentation as the comedo vestige.

15. The composition for preventing and treating skin diseases as claimed in claim 11, wherein the comedo vestige is topical cutaneous impression.

16. The composition for preventing and treating skin diseases as claimed in claim 12, wherein the comedo vestige is topical cutaneous impression.

17. The composition for preventing and treating skin diseases as claimed in claim 1, which is an agent for treating atopic skin diseases.

18. The composition for preventing and treating skin diseases as claimed in claim 2, which is an agent for treating atopic skin diseases.

19. The composition for preventing and treating skin diseases as claimed in claim 7, which is an agent for treating atopic skin diseases.

20. The composition for preventing and treating skin diseases as claimed in claim 8, which is an agent for treating atopic skin diseases.

21. The composition for preventing and treating skin diseases as claimed in claim 19, wherein the agent for treating atopic skin diseases is an agent for treating pigmentation as an atopic skin disease vestige.

22. The composition for preventing and treating skin diseases as claimed in claim 20, wherein the agent for treating atopic skin diseases is an agent for treating pigmentation as an atopic skin disease vestige.

23. The composition for preventing and treating skin diseases as claimed in claim 19, wherein the agent for treating atopic skin diseases is an agent for treating cutaneous impression as an atopic skin disease vestige.

24. The composition for preventing and treating skin diseases as claimed in claim 20, wherein the agent for treating atopic skin diseases is an agent for treating cutaneous impression as an atopic skin disease vestige.

25. The composition for preventing and treating skin diseases as claimed in claim 1, which is a wound healing agent.

26. The composition for preventing and treating skin diseases as claimed in claim 2, which is a wound healing agent.

27. The composition for preventing and treating skin diseases as claimed in claim 7, which is a wound healing agent.

28. The composition for preventing and treating skin diseases as claimed in claim 8, which is a wound healing agent.

29. The composition for preventing and treating skin diseases as claimed in claim 25, wherein the wound healing agent is an agent for healing pigmentation as a wound scar.

30. The composition for preventing and treating skin diseases as claimed in claim 26, wherein the wound healing agent is an agent for healing pigmentation as a wound scar.

31. The composition for preventing and treating skin diseases as claimed in claim 25, wherein the wound healing agent is an agent for healing keloid as a wound scar.

32. The composition for preventing and treating skin diseases as claimed in claim 26, wherein the wound healing agent is an agent for healing keloid as a wound scar.

33. The composition for preventing and treating skin diseases as claimed in claim 25, wherein the wound healing agent is an agent for healing wounds caused by scald or burn.

34. The composition for preventing and treating skin diseases as claimed in claim 26, wherein the wound healing agent is an agent for healing wounds caused by scald or burn.

35. The composition for preventing and treating skin diseases as claimed in claim 9, wherein the amount of the ascorbic acid derivative is in the range of 0.09 to 1 mol/L in terms of an ascorbic acid unit.

36. The composition for preventing and treating skin diseases as claimed in claim 10, wherein the amount of the ascorbic acid derivative is in the range of 0.09 to 1 mol/L in terms of an ascorbic acid unit.

37. The composition for preventing and treating skin diseases as claimed in claim 17, wherein the amount of the ascorbic acid derivative is in the range of 0.09 to 1 mol/L in terms of an ascorbic acid unit.

38. The composition for preventing and treating skin diseases as claimed in claim 18, wherein the amount of the ascorbic acid derivative is in the range of 0.09 to 1 mol/L in terms of an ascorbic acid unit.

39. The composition for preventing and treating skin diseases as claimed in claim 25, wherein the amount of the ascorbic acid derivative is in the range of 0.09 to 1 mol/L in terms of an ascorbic acid unit.

40. The composition for preventing and treating skin diseases as claimed in claim 26, wherein the amount of the ascorbic acid derivative is in the range of 0.09 to 1 mol/L in terms of an ascorbic acid unit.

41. The composition for preventing and treating skin diseases as claimed in claim 9, wherein the ascorbic acid derivative has been blended by means of phospholipid emulsification or liposome microencapsulation.

42. The composition for preventing and treating skin diseases as claimed in claim 10, wherein the ascorbic acid derivative has been blended by means of phospholipid emulsification or liposome microencapsulation.

43. The composition for preventing and treating skin diseases as claimed in claim 17, wherein the ascorbic acid derivative has been blended by means of phospholipid emulsification or liposome microencapsulation.

44. The composition for preventing and treating skin diseases as claimed in claim 18, wherein the ascorbic acid derivative has been blended by means of phospholipid emulsification or liposome microencapsulation.

45. The composition for preventing and treating skin diseases as claimed in claim 25, wherein the ascorbic acid derivative has been blended by means of phospholipid emulsification or liposome microencapsulation.

46. The composition for preventing and treating skin diseases as claimed in claim 26, wherein the ascorbic acid derivative has been blended by means of phospholipid emulsification or liposome microencapsulation.

* * * * *